(12) United States Patent
Zalevsky et al.

(10) Patent No.: US 8,638,991 B2
(45) Date of Patent: Jan. 28, 2014

(54) MOTION DETECTION SYSTEM AND METHOD

(75) Inventors: Zeev Zalevsky, Rosh HaAyin (IL); Javier Garcia, Valencia (ES)

(73) Assignees: Bar Ilan University, Ramat Gan (IL); Universtitat de Valencia, Valencia (ES)

( * ) Notice: Subject to any disclaimer, the term of this patent is extended or adjusted under 35 U.S.C. 154(b) by 698 days.

(21) Appl. No.: 12/670,477

(22) PCT Filed: Jul. 21, 2008

(86) PCT No.: PCT/IL2008/001008
§ 371 (c)(1),
(2), (4) Date: Jan. 25, 2010

(87) PCT Pub. No.: WO2009/013738
PCT Pub. Date: Jan. 29, 2009

(65) Prior Publication Data
US 2010/0226543 A1  Sep. 9, 2010

(30) Foreign Application Priority Data

Jul. 26, 2007  (IL) .......................................... 184868

(51) Int. Cl.
*G06K 9/00* (2006.01)
(52) U.S. Cl.
USPC .............. 382/107; 348/169; 704/200; 702/56
(58) Field of Classification Search
USPC ......... 382/100, 103, 106, 107, 128, 129, 130, 382/131, 132, 181, 190, 195; 348/169–172; 704/200–504; 73/1.48, 1.82, 54.41; 702/54, 56; 381/56; 372/4; 375/316, 375/325

See application file for complete search history.

(56) References Cited

U.S. PATENT DOCUMENTS

| | | | |
|---|---|---|---|
| 3,804,521 A | 4/1974 | Sprague | |
| 3,952,583 A | 4/1976 | Rosati | |
| 5,481,356 A * | 1/1996 | Pouet et al. | 356/35.5 |
| 5,616,839 A * | 4/1997 | Chen et al. | 73/146 |
| 6,545,762 B2 * | 4/2003 | Lewis et al. | 356/502 |
| 2004/0061680 A1 * | 4/2004 | Taboada | 345/157 |
| 2005/0210982 A1 | 9/2005 | Pepper et al. | |
| 2006/0215244 A1 * | 9/2006 | Yosha et al. | 359/15 |
| 2007/0071295 A1 * | 3/2007 | Jackson | 382/128 |

(Continued)

FOREIGN PATENT DOCUMENTS

| WO | 2005/090908 A1 | 9/2005 |
| WO | 2007/054861 A2 | 5/2007 |
| WO | 2007/113810 A1 | 10/2007 |

OTHER PUBLICATIONS

D.A. Gregory, "Basic physical principles of defocused speckle photography: a tilt topology inspection technique", Optics and Laser Technology, pp. 201-213 (Oct. 1976). Cited in IDS and supplied by applicant.*

(Continued)

*Primary Examiner* — Anand Bhatnagar
(74) *Attorney, Agent, or Firm* — The Law Office of Michael E. Kondoudis

(57) ABSTRACT

A method is presented for imaging an object. The method comprises imaging a coherent speckle pattern propagating from an object, using an imaging system being focused on a plane displaced from the object.

40 Claims, 9 Drawing Sheets

(56) References Cited

U.S. PATENT DOCUMENTS

| | | | |
|---|---|---|---|
| 2008/0015428 A1* | 1/2008 | Epstein et al. | 600/410 |
| 2010/0061562 A1* | 3/2010 | Segev et al. | 381/71.4 |
| 2012/0237104 A1* | 9/2012 | Fouras et al. | 382/132 |

OTHER PUBLICATIONS

D.A. Gregory, "Basic physical principles of defocused speckle photography: a tilt topology inspection technique", Optics and Laser Technology, pp. 201-213 (Oct. 1976).

J. M Diazdelacruz, "Multi-windowed defocused electronic speckle photographic system for tilt measurements", Applied Optics, vol. 44, No. 12, pp. 2250-2257 (Apr. 2005).

M. Sjodahl, "Calculation of Speckle Displacement, Decorrelation, and Object-Point Location in Imaging Systems", Applied Optics, vol. 34, No. 34, pp. 7998-8010 (Dec. 1995).

M. Sjodahl, "Electronic Speckle Photography: Measurement of In-Plane Strain Fields Through the Use of Defocused Laser Speckle", Applied Optics, vol. 34, No. 25, pp. 5799-5808 (Sep. 1995).

EP Communication dated Jul. 16, 2012, received in EP Application No. 08776638.2.

International Search Report dated Nov. 13, 2008 in corresponding International Application No. PCT/IL2008/001008.

* cited by examiner

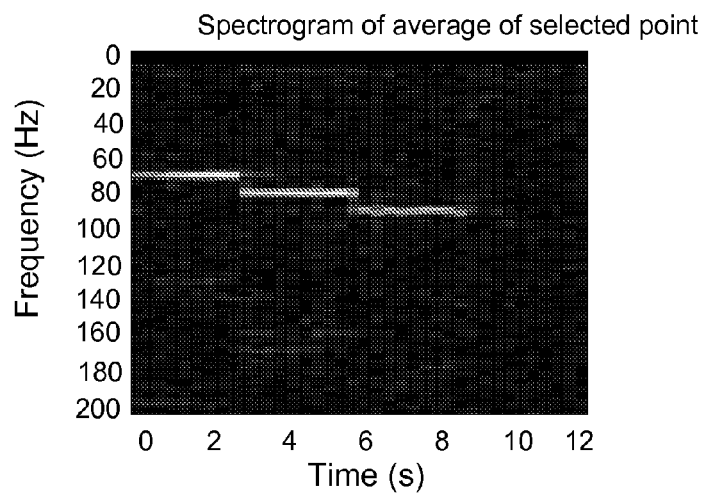
FIG. 2C
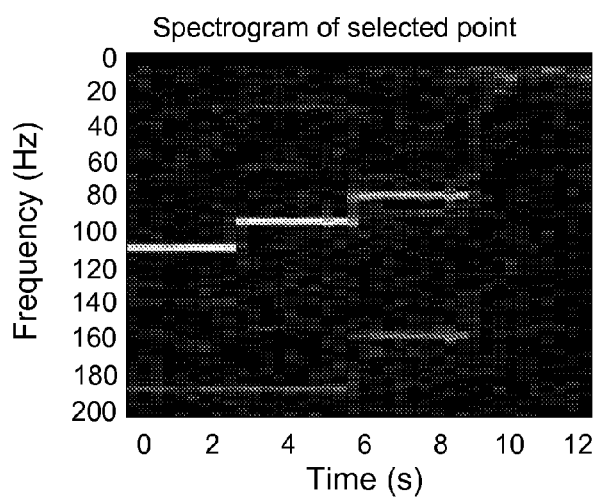
FIG. 2D
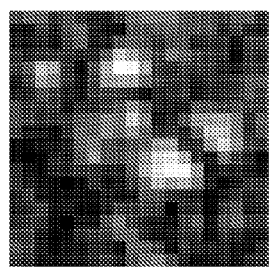 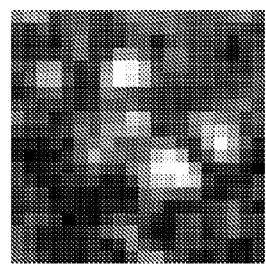 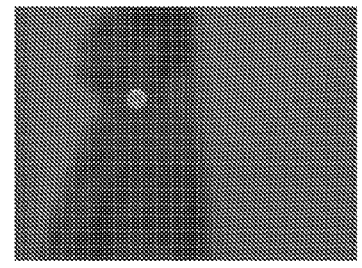
FIG. 3A	FIG. 3B	FIG. 3C

MOTION DETECTION SYSTEM AND METHOD

CROSS REFERENCE TO RELATED APPLICATIONS

This application is a National Stage of International Patent Application No. PCT/IL2008/001008, filed Jul. 21, 2008, which claims the benefit of Israeli Patent Application No. 184868, filed Jul. 26, 2007.

FIELD OF THE INVENTION

This invention is in the field of motion detection and recognition. It is particularly useful for detection and recognition of motions associated with various sounds, for example heart beats and speech.

BACKGROUND

Motion identification is useful in a very broad range of applications, including for example manufacturing production control, surveillance, and biomedical applications. Various methods have been developed by which motion can automatically be identified including mechanical, electronical, optical and acoustical motion detection.

For example, optical motion detection can be performed by a speckle-based technique, such as electronic speckle-pattern interferometry (ESPI). The ESPI has been used for displacement measurements and vibration analysis, aimed at amplitudes, slopes and modes of vibration. Speckle-based techniques have also been used for deformation measurement. The optical detection can be the only viable option if the environment of a moving object hinders sound propagation or unpredictably alters it.

The acoustical detection is especially useful in environments preventing light propagation from a moving object to an observer. For acoustical detection, the motion to be detected needs to be associated with a sound. However, the moving object's environment may not allow propagation of sound beyond a certain distance range. In particular, this occurs when sounds are produced behind a window (e.g. inside of a room). Likewise, motion of interest may be associated with sounds which may be remote or weak. If for any reason sounds decay before they reach a remote observer, sound detection should be indirect. This indirect detection may be based on optical means.

In particular, considering the example of sounds produced behind a window, they may be detected by detection of a laser beam reflection from the window. For generation of the reflection, the laser beam may be projected on the window. The reflection detection may be performed by an optical interferometer. The sounds then can be extracted (recognized) by processing the interferometer's output electronic signal. The interferometer's output is indicative of sounds produced behind the window because sounds vibrate the latter and phase-modulate the reflection of the laser beam. However, in this interference-based sound detection technique all sounds vibrating the window participate in the phase-modulation. Consequently, they are detected in sum (i.e. as superposition) and for their separation a blind source separation procedure needs to be performed. Also, in this technique, the projection laser and the detection interferometer module need to be placed in such a way that the specularly reflected beam is directed towards the detection module. This interference-based technique requires complicated calibration before the operation and error control during the operation.

Motion detection is useful in biomedical applications. For example, it can be used for detection and controlling Coronary Heart Disease (CHD). The CHD, along with Congestive Heart Failure, is connected with the regional and global motion of the left ventricle (LV) of the heart: CHD typically results in wall-motion abnormalities. For example, if local segments of the LV wall move weakly, this condition is known as hypokinesia; if they do not move at all, this condition is akinesia; and if they move out of sync with the rest of the heart, this condition is dyskinesia. Sometimes motion in multiple regions, or the entire heart, is compromised. The beats of LV can be imaged in a number of ways. The most common method of this is the echocardiogram—a test that uses sound waves to create a moving picture of the heart. In this test, high-frequency sound waves are emitted by a transducer placed on patient's ribs near the breast bone and directed toward the heart. The echoes of the sound waves are picked up and transformed as electrical impulses to an echocardiography machine. The machine converts these impulses into moving pictures of the heart.

Heart beats can be monitored by other methods, especially if less detailed picture is needed. For example, for the detection of heart rate and pulse there are three main techniques in use: (1) detecting blood flow in the capillaries of a finger or ear lobe with an infrared sensor; (2) detecting the heart ECG electrical signal in the hand area; and (3) detecting the heart ECG electrical signal with chest electrodes, commonly attached to an elastic strap going around the chest. A timing circuit measures the interval between each beat, averages the intervals for a short period of time and converts this into a heart rate reading expressed in beats per minute. Typically, a user of a heart rate monitor must stop exercising and hold his or her finger on the sensor and be very still, while measuring.

DESCRIPTION

There is a need in the art of a novel optical motion detection technique, capable of indirect detection of sound and speech. A presented here novel technique, developed by the inventors, and based on optical imaging, has adaptations (versions, embodiments) useful for such detection. The technique is useful for detections of motions containing a tilt component.

The technique includes imaging of a coherent speckle pattern formed by an object or subject or, generally, a surface of interest. The pattern can be formed by illumination of the still or moving surface of interest by coherent light of a laser or another light source. Preferably, the surface movement includes a tilt component. The surface movement can be for example of vibration type. The vibration can be caused by a sound or vibration itself can produce a sound, thus making the motion of the surface of interest associated with the sound. The motion of the surface of interest is further termed herein motion of interest.

In the inventors' technique, the imaging employs focusing on a plane or surface being between the moving surface and an imaging unit (light detecting surface) or on a plane or surface being behind the moving surface. Such planes or surfaces are termed herein displaced planes. Planes being between the moving surface and the imaging unit are termed herein forward displaced planes; and planes being beyond the moving surface, looking from the imaging unit, are called herein downward displaced planes. In some embodiments, the imaging utilizes focusing on a forward displaced plane being in the far field from the moving surface. Such planes or surfaces are termed herein far field forward displaced planes. In some other embodiments, the imaging utilizes focusing on a downward displaced plane being in the far field from the moving surface. Such planes or surfaces are termed herein far field downward displaced planes. While some of the considerations below directly address the case of imaging that employs focusing on forward displaced planes or far field forward displaced planes, these considerations can be appropriately applied to the case of using focusing in downward displaced or far field downward displaced planes.

The inventors have found that at forward displaced planes a coherent speckle pattern associated with the surface of interest becomes generally stationary, and at far field forward displaced planes the coherent speckle pattern becomes even more stationary (substantially stationary). The stationarity is in fact quasi-stationarity (approximate stationarity); it appears at forward displaced planes if the surface of interest, while moving, keeps its shape constant or changes this shape relatively slowly. The (quasi) stationarity of the speckle pattern effectively restricts the speckle pattern variation to shifting in correspondence with the motion of interest. This effect is most evident at the far field forward displaced planes. This effect is not used in typical imaging techniques, utilizing focusing on the surface of interest.

It should be noted that the technique of the invention can be used for extraction of motion even in cases when only a certain region of the surface of interest keeps its shape constant or changes its shape quasi-stationary: if a motion or sound to be detected is associated with the whole surface of interest, then this motion or sound can be extracted from the motion of this region.

The stationarity also appears for downward displaced planes and far field downward displaced planes. The speckle pattern may not reach these planes because the object separates them from speckle pattern's origin; for example the speckle pattern will not reach these planes if the object (surface of interest) is opaque. This, however, does not preclude imaging with focusing on one of these downward displaced and far field downward displaced planes. The imaging unit focused at a downward displaced plane will still receive the speckle pattern originated from the object, not from the downward displaced plane. This pattern will result in an image that would be produced by a converging speckle pattern originating from the downward displaced plane, propagating through the speckle pattern's true birth spot, and diverging starting from this spot, despite that in fact the speckle pattern would originate from the coherent light illuminated spot (i.e. its birth spot).

It should be noted that focusing on a downward displaced or far field downward displaced plane may be very useful when the imaging unit is too close to the surface of interest: if imaging unit requires too specialized details (e.g. lenses) and/or if the imaging surface is not in the far field of the object of interest (far field of the speckle pattern original spot). The imaging unit then may be focused at a downward displaced plane being in the far field of the surface of interest; stationarity property will appear thanks to the principle of reversibility of light.

Considering the use of the stationarity, the motion of interest (or the motion of the certain region of the surface of interest) can be extracted from spatio-temporal trajectories of speckles. The extraction can be based on motion estimation (ME) techniques including those based on block matching algorithm (BMA), parametric/motion models, optical flow, and pel-recursive techniques. The extraction is facilitated due to the speckle pattern stationarity. When the latter is present, it allows identifying the surface of interest (or at least a region of the surface of interest) in different frames and considering the motion of this surface of interest (or at least of the region of the surface of interest) as motion of a rigid body. Therefore, the stationarity allows tracking a certain region of the surface of interest or the entire surface of interest, and extracting from its motion a special type of motion, for example, oscillatory motion associated with sound. It should be noted, that it occurs quite frequently, that the motion of interest is a superposition of various motions, one or more of which is/are of a special type, e.g. of vibration type, pertinent to the application in which the surface is used.

The technique of the present invention allows, for example, detection of sounds produced by a remote source. These sounds may be distorted or weak when they reach an observation point or may not reach such a point at all. The sounds can be associated with surfaces the motions of which include movements besides the sound vibrations. The technique also allows separate detection of several sounds, which is useful when two or more sounds are produced simultaneously. In fact, different sound sources may be imaged by different regions of a pixel detector array (PDA) of an imaging unit. Thus, the technique is useful for example for extracting speech of several persons speaking at the same time. Accordingly, the typically present in acoustical techniques need for the blind source separation becomes reduced or absent. As well, the technique of the present invention is useful for extracting speech of even one person in a noisy environment, present for example in a nightclub or in nature in case of respective weather conditions.

The technique of the invention is interference-based, but it does not require an interferometer: a speckle pattern generated at a surface illuminated by a spot of laser beam (the so-called "secondary speckle pattern") is actually a localized self-interfering pattern. In coherent speckle patterns each individual speckle serves as a reference point from which changes in the phase of light can be tracked.

The technique of the present invention also provides a leeway for positioning an imaging unit relatively to the moving surfaces (e.g. surfaces of sound sources or surfaces of objects experiencing sound-caused vibrations). The leeway is due to the divergence of the speckle pattern: speckles are due to diffuse reflection and they are formed spatially small (initially their size is of about the optical wavelength), therefore their diffraction occurs in a wide angle (close to $2\pi$ steradians). Consequently, independently on a location of the imaging unit, but provided that the imaging unit is correctly oriented, it can collect speckles. However, for the extraction of motion, the imaging unit location in the far field of the surface of interest is preferred.

The inventors have considered applications of their technique for detection of various motions, including those associated with sounds, such as speech and heartbeats. For detection of speech the inventors have imaged speckle patterns formed by reflection of coherent infrared light from a human body, in particular from human head, cheeks, cheekbones, or throat. For facilitation of the detection of speech, the imaging unit has been operated with a sampling rate of 10 KHz, i.e. with a sampling rate larger than 8 KHz, the average Nyquist frequency of speech. The Nyquist frequency of speech may be lower, therefore in various embodiments of this technique, the imaging unit sampling rate may be for example between 2 KHz and 4 KHz, or 4 KHz and 8 KHz, or higher than 8 KHz.

A motion detection system may include an imaging unit, an illumination unit (e.g. a laser), and an extraction unit (e.g. a computer programmed to extract speech or heart beat vibrations from spatio-temporal trajectories of the speckle-pattern, or an application-specific integrated circuit, ASIC, configured to extract vibrations). The imaging unit may include PDA and optics adapted for imaging the relevant speckle pattern. The PDA and optics may have one or more of its characteristics, such as resolution, pixel size, aperture size and focal length, determined by or limited by an expected object distance (i.e. an expected distance from the imaging unit to the surface of interest).

For example, when a surface associated with speech is located relatively far away, the speckle pattern reaching an in-focus forward displaced or far field forward displaced plane may be large: the scale of the speckle pattern generated at the surface of interest increases proportionally to a distance from the surface of interest. An objective (e.g. one or more lens) of the imaging unit projects the speckle pattern onto the PDA and typically demagnifies the scale of the speckle pattern. The imaging unit is to be configured so at to collect a sufficient number of speckles within the imaged speckle pattern and so as to resolve the speckles in the collected pattern. Therefore, the aperture of the objective of the imaging unit is to be selected sufficiently large for collecting at least several speckles from a speckle pattern propagating from the remote surface of interest. The focal length of the objective is to be selected sufficiently large and the pixel size of the PDA is to be selected sufficiently small for resolving the speckles of the collected speckle pattern. Possible selections of the optics and PDA parameters depend on the motion detection system application.

The selection of the imaging unit parameters can depend also on additional factors such as a size of the coherently illuminated spot on the surface of interest, desired PDA frame rate and sensitivity, an available PDA size or pixel count. For example, the size of the coherently illuminated spot is related to the PDA frame rate and PDA pixel size and count. In fact, if between two frames the surface of interest moves too much, there might be no region of this surface that would be illuminated and imaged in both frames: the illuminating light might fall onto a completely new region of this surface during the imaging of the second frame or even not fall on this surface at all, or speckles reflected from the intersection of the two illuminated regions might miss the imaging unit during the imaging of the second frame. The latter case can for example occur if the reflection from the illuminated intersection of two regions moves outside the PDA. Therefore, the size of the coherently illuminated spot, dependent on a cross-section of the illuminating beam, can be made smaller, if the PDA frame rate is made larger. In general, a product of these two parameters is larger if an expected speed of the motion of interest is larger. Similarly, in general, the PDA pixel count has to be larger if expected amplitude or expected region of the motion of interest is larger. It should be noted, however, that in some embodiments the illuminating beam and/or imaging unit can be operated to follow the certain region of the surface of interest and/or the speckles generated at this region.

In accordance with the above, the parameters of the motion detection system can be optimized for various applications. For example, if a PDA of a relatively high frame rate is needed in the imaging unit, the operational wavelength of the motion detection system can be made relatively short, i.e. the wavelength can be from the visible spectrum rather than from the infrared. This relates to the fact that, typically, PDAs for infrared light are slower than PDAs for visible light. Also, optics is typically larger for infrared light.

The choice of the motion detection system operational wavelength can be based also on a desired covertness of the illuminating beam and on a desired safety of use of the illuminating beam. For example, wavelength of illuminating light can be chosen to be outside the visible spectrum.

Considering types of motion that can be detected by the technique of the invention, the following should be noted. Generally, a motion of a surface can be split into such components as transversal motion, axial motion, and tilt (the axis connects the surface of interest with the imaging unit). The technique of the invention has an enhanced sensitivity to the tilt, which on the imager sensing plane (PDA) primarily causes speckle pattern shifting. The transversal motion of the surface of interest causes shifts and changes of the speckle pattern image, but in cases when imaging utilizes focusing on a displaced (e.g. forward or downward displaced) plane thus caused shifts are often significantly smaller than the shifts caused by the tilt. Moreover, if the displaced (e.g. forward displaced) plane is in the far field of the speckle pattern source spot, these shifts become suppressed: the effect of the transversal motion becomes restricted mostly to a change of the speckle pattern phase. The third motion component, the axial motion, causes scaling of the speckle pattern. However, in many applications axial coordinate of the surface of interest changes only slightly relatively to an axial distance between the imaging unit and the surface of interest; axial motion thus may or may not significantly affect the speckle pattern image. As a result, the technique of the invention is primarily useful for extraction of the tilting motions, though determination of a trajectory of the surface of interest is not precluded, even when the motion of interest has all three named components.

In this connection, it should be understood that in some applications extraction of all motion components is not required. For example, the inventors experimented with human speech extraction. In most cases, the obtained speech was recognizable despite that the extraction had been performed using an assumption that the speckle pattern had moved only as a result of the tilt (the assumption was not in fact required).

The inventors have also experimented with vibrations of body parts. In these experiments, they contactlessly detected heart beats of experiment participants. The obtained heart beats were repeatable for the same participant and differed from participant to participant. The inventors then developed a concept of optical cardiogram (OCG). OCG can be used for determining health conditions, for authentification, in lie detectors.

There is thus provided, according to one broad aspect of the invention, a method of imaging an object. The method includes imaging a coherent speckle pattern, propagating from the object, by an imaging system being focused on a plane displaced from the object.

The displaced plane may be located between the imaging system and the object; or further from the imaging system than the object.

For example, the displaced plane may be located further than $D^2/4\lambda$ from the object, D and $\lambda$ being respectively a size and a wavelength of the speckle pattern at the object. This plane is thereby in a far field of the object.

In some embodiments of the invention, illumination of the object with coherent light is used to form the coherent speckle pattern.

The imaging method may be used for imaging the object while moving. The movement may be associated with a vibration, e.g. of a living body's part.

The vibration may correspond to a speech, a sequence of heart beats, a heart beat resolved to a heart beat's structure, as well as vibration of a cloth on a living body.

The living body's part may be at least one of a hand joint, a chest, a throat, a temporal fossa, a stomach, a throat, a cheekbone, a head.

In some other embodiments of the invention, the vibration of a vehicle's (e.g. car's) part is detected. The vehicle's part may be an interior part, e.g. a part of vehicle's engine; or an exterior part.

Preferably, the imaging is repeated at least two times for obtaining a sequence of at least two speckle pattern images.

For example, the method may include extracting the speech from a sequence of images of a living body part, extracting the sequence of heart beats, extracting the heart beat's structure. The method may include comparing the extracted heart beat's structure with a heart beat's structure of the same heart; comparing the extracted heart beat's structure with a heart beat's structure of a different heart.

The method may be used in motion detection. To this end, a shift between regions of an object which appear in first and second images of the object is determined. Each of these regions includes a stationary speckle pattern formed by light originated at the same region of the object and imaged by focusing on a plane which is displaced from the object and located in a far field of the object.

Preferably, the shift determination is repeated at least two times so as to obtain a sequence of shifts. In some embodiments of the invention, the obtained sequence of shifts is compared with another sequence of shifts.

According to another broad aspect of the invention, there is provided a method for use in motion detection. The method includes determining a shift between regions of an object which appear in first and second image of the object, each of the regions including a stationary speckle pattern formed by light originated at the same region of the object and image by focusing on a plane which is displaced from the object and is located in a far field of the object.

According to yet another broad aspect of the invention, there is provided a system for use in motion detection. The system includes a source of a beam of coherent light and an imaging system, the imaging system being capable of being focused on a plane displaced from an intersection of the beam and a field of view of the imaging system and being in a far field from the intersection.

The focusing (in-focus) plane may be located between the imaging system and the intersection location; or further from the imaging system than the intersection location.

The detection system may include a processing unit associated with said imaging system. The processing unit is configured and operable to determine a shift between two images of a speckle pattern originated at the intersection location.

In its yet further aspect, the invention provides a memory (technical memory) including data indicative of a sequence of images of a stationary coherent speckle pattern originated at a subject, the data being indicative of the subject's heart beats and/or heart beat structure, the sequence being thereby enabled for use in determination of at least one physiological parameter.

The at least one physiological parameter may include at least one from the following: a heart beat rate, heart beat structure, and optical cardiogram.

The stored data may include the sequence of images of the stationary coherent speckle pattern originated at the subject; or a sequence of shift values between the images in the sequence of images of the stationary speckle pattern originated at the subject, the shift values being indicative of the subject's heart beat rate.

The sequence may include an image of at least one of a hand joint, a chest, a throat, a temporal fossa.

In yet further aspect, there is provided a memory including data indicative of a sequence of images of a stationary speckle pattern originated at a subject, said sequence being indicative of the subject's speech.

The stored data may include the sequence of images of the stationary speckle pattern; or a sequence of shift values between the images of the stationary coherent speckle pattern, the sequence being indicative of the speech. The sequence may be taken with a rate between 2 and 4 KHz; a rate between 4 KHz and 8 KHz; a rate exceeding 8 KHz. The sequence may include an image of at least one of a throat, a cheekbone, a head.

There is also provided a memory including data indicative of a sequence of images of a stationary speckle pattern originated at a vehicle, the images being indicative of vibrations associated with the vehicle and the sequence being indicative of the vehicle operation.

The stored data may be indicative of an image of a region of the vehicle's interior, e.g. vehicle's engine; and/or an image of a region of the vehicle's exterior.

The invention also provides a device comprising the above-described memory, and one or more processors configured for determining a sequence of shift values between the images in the sequence of images of the stationary speckle pattern; and/or a spectrogram of a sequence of shift values between the images in the sequence of images of the stationary speckle pattern. The device might be configured as or include a computer (e.g. programmed computer).

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 2A-2D illustrate respectively the following: (A) The image of the loudspeakers; (B) Graph of evolution of speckle pattern position captured from the left loudspeaker; (C) The reconstructed spectrogram of the left loudspeaker; (D) The reconstructed spectrogram of the right loudspeaker.

FIGS. 3A-3G illustrate the following: (A)-(B) Two sequentially captured speckle patterns; (C) The defocused image of an experiment participant and of a speckle pattern propagating from the participant's throat; (D) Two examples of evolution of the speckle pattern position; (E) Zoomed one of the two previous examples, along with smoothed graph of evolution of the speckle pattern position; (F) Vibrations extracted from the previous example of evolution of the speckle pattern position; (G) Spectrogram of a speech signal (a scream) corresponding to the vibrations of the previous example.

DETAILED DESCRIPTION OF EXEMPLARY EMBODIMENTS

Figure 1:
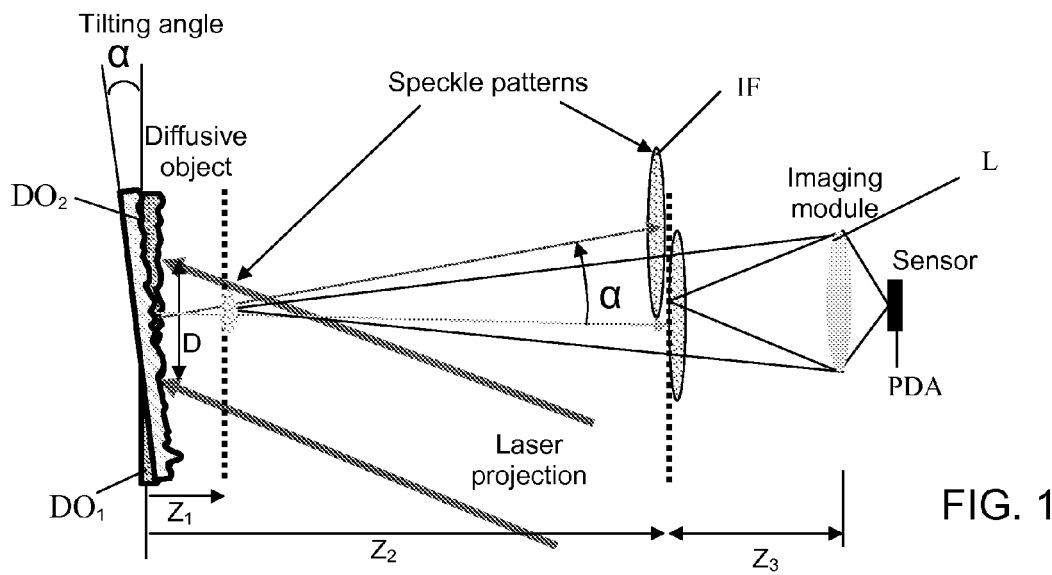
FIG. 1 is a schematic illustration of an imaging system utilizing the principles of the present invention.

Referring to FIG. 1, there is schematically illustrated an imaging process of a secondary speckle pattern generated at a surface of a moving diffusive object. Imaging is performed by an imaging unit 10 at two instances: when the diffusive object is at a position and orientation $DO_1$ and when the diffusive object is at a position and orientation $DO_2$. The imaging unit 10 includes an imaging lens L and a pixel detector array PDA. The imaging unit is configured for focusing on a forward displaced plane IF. At both instances, the speckle pattern is formed as a reflection of coherent light beam LB (e.g. laser beam). The speckle pattern propagates to the in-focus plane, where it takes a form $SP_{IF,1}$ in the first instance and a form $SP_{IF,2}$ in the second instance. The speckle pattern continues to propagate: it crosses the in-focus plane and reaches the imaging unit, so that a portion of the speckle pattern gets collected by the imaging lens. For assessing and using a variation between speckle patterns imaged at different instances, the inventors have used a model according to which the object surface shape illuminated by the laser beam spot is not changed in time interval between two frames (i.e. is not changed between two subsequent imaging instances). In other words, the object surface shape has been assumed to be stationary (e.g. rigid).

With regards to speckle patterns the following should be noted. Speckle patterns are self interfered random patterns having relatively random amplitude and phase distributions. So-called "primary speckle patterns" can be generated by passage of illuminating light through a diffuser or a ground glass. So-called "secondary speckle patterns" can be generated by reflection of illuminating light from the diffuse surface of an object.

A movement of a rigid object surface can be presented as a superposition of basic movements of three types: transverse, axial, and tilt. Typically, all three of these components will be present in the superposition. However, these movements are translated differently on the PDA plane. The inventors have found that, due to the forward displaced positioning of the in-focus plane of the imaging unit, tilt tends to produce the major effect on the speckle pattern and this effect tends to be in the speckle pattern shifting.

In fact, considering the effects of the three components one by one, the following is noted. The first, transverse, component of the object movement is manifested in the transverse shifting of the forming speckle pattern. This shift is demagnified by the imaging unit after projection of the speckle pattern on the image plane (PDA plane). The transverse shift of the projected on the PDA speckle pattern can be expressed through a causing this shift transverse shift $\Delta X$ of the object: the shift of the pattern equals $\Delta X/M$, where a demagnification factor M equals $(Z_2+Z_3-F)/F$, $Z_2$ is a distance between the object and the in-focus plane, $Z_3$ is a distance between the in-focus plane and the lens, and F being a focal length of the lens. The shift can be written also as $\Delta X F/(Z_t-F)$, $Z_t=Z_2+Z_3$ being a total distance from the lens to the object. If the imager (imaging unit) is focused at a plane being in the far field of the original speckle pattern spot, the effect of the transverse component reduces to a change of the phase of the speckle pattern.

The second, axial, component of the object's movement, is manifested in a change of a scale of the imaged speckle pattern. This change is relatively small, as it is demagnified by the imaging unit. In terms of FIG. 1, while for the object being in position $DO_1$ demagnification factor equals $M=(Z_2+Z_3-F)/F$, for object in position $DO_2$ this factor will equal $(Z_2+Z_3+\Delta Z-F)/F$, $\Delta Z$ being an axial shift between position $DO_1$ and $DO_2$. The relative change of the demagnification factor will equal $(Z_2+Z_3+\Delta Z-F)/(Z_2+Z_3-F)-1$. The relative change can be written also as $(Z_t+\Delta Z-F)/(Z_t-F)-1=\Delta Z/(Z_t-F)$.

Incidentally, the third, tilt, component of the object motion affects the speckle pattern similarly to the first, transverse, component of the object motion: as a result of the tilt the speckle pattern in the PDA plane shifts. However, in counter distinction with the shift caused by the transverse component, the shift caused by the tilt becomes more important when the imaging unit is focused on a plane closer to the imaging unit and further from the object, as the latter shift equals $Z_2\Delta\alpha/M_{IF}=Z_2F\Delta\alpha/(Z_3-F)$, $\Delta\alpha$ being the tilt, $M_{IF}$ being a demagnification factor for plane IF. This shift can be written also as $(Z_t-Z_3)F\Delta\alpha/(Z_3-F)$.

It can be seen from the above, that imaging the speckle pattern with focusing on a forward displaced plane and with focusing on the object leads to different results. While in the latter case the relevant condition $Z_3 \approx Z_t$ results in that a motion of a remote object (i.e. for which object distance $Z_t \gg F$) may not translate into a significant motion of the speckle pattern, even if the motion has all three components, in the former case the relevant condition $Z_3 < Z_t$ results in that the speckle pattern on the PDA plane can move a distance useful for detection, if the motion has a tilt component. In other words, it can be concluded that even a slight movement of the object can be magnified to significant shifts in the PDA plane if the movement contains tilt component, the object is sufficiently far from the imaging unit, and the in-focus plane is sufficiently close to the imaging unit. Imaging the speckle pattern with focusing on an object leads rather to a change of the speckle pattern than to its shift when the object moves.

It should be noted, that increasing focal length F up to values close to object distance $Z_t$ might magnify the lateral shift in the PDA plane to significant values in the case of the imaging unit being focused on the object. However, this would typically require increasing an objective length to overly large values. Indeed, in the case of objective consisting of a single lens, the objective length, i.e. the length between lens L and pixel detector array PDA, equals $Z_tF/(Z_t-F)$. If focal length F would be close to object distance $Z_t$, and the object would be relatively remote, the objective length might need to be very large.

In the case of the imaging unit being focused on a forward displaced plane, the task of magnifying lateral shift may be fulfilled somewhat similarly, by the selection of the position of the forward displaced imaged plane close to a focal plane (i.e. by selecting $Z_3 \approx F$). However, in this case the focal length does not have to be close to object distance $Z_t$; and therefore while an increase in the objective length may be needed, this increase generally may be smaller.

The case of the imaging unit focused on a downward displaced plane can be considered similarly to the case of the imaging unit focused on a forward displaced plane.

As it is clear from above, the inventors' technique provides a convenient for measuring shift of a speckle pattern generated at the object's surface. The shift can be provided by focusing the imaging unit on a plane being closer to the imaging unit than the object or being further from the imaging unit than the object. Particularly, the imaging unit may be focused on a plane being in the far field of the object. The inventors also considered selection of other parameters of the detection system.

For example, the invented motion detection technique can employ tracking of the speckle pattern or of a region of the speckle pattern through a number of images (frames). Tracking may follow intensity maxima of the speckle pattern. In such a case these intensity maxima need to be resolved by the imaging system.

As it is known, at a distance $Z_2$ from the speckle-forming spot of a size D an average speckle size reaches $\lambda Z_2/D$. Herein $\lambda$ is a wavelength of light.

A resolution of the speckle pattern imaged at the sensor plane (i.e. the PDA plane) equals (in the case of imaging focused at a front removed plane):

$$\delta x = \frac{\lambda Z_2}{D} \cdot \frac{1}{M_{IF}} = \frac{\lambda F}{D} \cdot \frac{Z_2}{Z_3 - F} \quad (1)$$

In some embodiments, this resolution is larger (and therefore is not limited by) than the optical and the geometrical resolution of the imaging unit. In particular, in some embodiments, the PDA has a pixel size p smaller than one, or a half, of the average speckle δx. If the pixel size p is K times smaller than the average speckle, then a typical speckle will be sensed by K pixels in the PDA plane. The latter condition can be written as:

$$F = \frac{Kp(Z_3 - F)D}{Z_2 \lambda} \quad (2)$$

In some embodiments, it can be approximated as $$F \approx \frac{KpZ_3 D}{Z_2 \lambda} \quad (3)$$

The latter approximation is useful in particular in those cases in which the objective length is selected to be relatively small; for example only slightly larger than the focal length F.

Further, in some embodiments, it can be approximated as $$F \approx \frac{KpZ_3 D}{Z_t \lambda} \quad (4)$$

Approximation (4) is useful when the imaging system is configured for detection of relatively small object tilts which need the highest possible magnification, but without a significant increase in the objective length.

Imaging the same speckle with more than four pixels may be redundant. Therefore, in some embodiments, the pixel size is larger than a quarter of the averaged speckle size.

For speckle pattern tracking, a number of speckles collected by the PDA in every dimension needs not be too small, otherwise a correspondence between speckle patterns from different frames might not be established. The number of collected speckles in a single dimension of the PDA equals:

$$N = A \frac{Z_2}{Z_t} \frac{1}{M_{IF} \delta x} = \frac{AD}{\lambda Z_t} = \frac{FD}{F_\# \lambda Z_t} \quad (5)$$

Here A is a diameter of the aperture of the lens, in the respective dimension; $F_\#$ is an F-number of the lens. The latter relation is obtained thanks to large divergence of the speckle pattern, making the aperture of the lens to be filled with the speckles. In some embodiments, the number of speckles N is larger than 2 and smaller than 4. In some other embodiments, the number of speckles N is larger than 4 and smaller than 8. Yet in some other embodiments, the number of speckles N is larger than 8 and smaller than 10. Yet in some other embodiments, the number of speckles N is larger than 10 and smaller than 16. Yet in some other embodiments, the number of speckles N is larger than 16 and smaller than 20, or larger than 20.

The pixel count of the PDA, in any dimension, may need to be larger than KN. For example, in some embodiments it is larger 2 times than 20, i.e. larger than 40.

The tracking of the speckle pattern may be facilitated if the speckle pattern is stationary or quasi-stationary, i.e. if it mostly shifts in the PDA plane, without significantly changing its topology and scale. The (quasi-) stationarity can be provided if the in-focus plane is in the far field of the speckle-forming light spot. For example, some quasi-stationarity may be provided if the distance $Z_2$ between the speckle-forming light spot and the in-focus plane is larger than $D^2/4\lambda$.

The origin of the far field condition can be clarified by comparing imaging of the speckle pattern with focusing close and far from the speckle-forming spot. The field formed by the speckle pattern needs to be considered in detail. It may be assumed that the object surface adds to the phase of coherent illuminating field a random phase distribution φ(x,y), (x,y) being coordinates at the surface of the diffusive object.

Considering first a case of the imaging unit utilizing focusing onto a plane close to the speckle-forming spot, for a plane being in the close field of the object (at a small distance $Z_1$ from the object) the light field distribution is:

$$T_m(x_o, y_o) \propto \int\int \exp[i\phi(x, y)]\exp\left[\frac{\pi i}{\lambda Z_1}((x - x_0)^2 + (y - y_0)^2)\right]dxdy \propto \quad (6)$$
$$A_m(x_o, y_o)\exp[i\psi(x_o, y_o)]$$

The above field $T_m(x_o, y_o)$ has spatially non-uniform amplitude $A_m(x_o, y_o)$ and phase $\Psi(x_o, y_o)$, where $(x_o, y_o)$ are coordinates in the plane close to the object. The field $T_m(x_o, y_o)$ is calculated as a Fresnel integral for the random phase φ, introduced by the surface of the diffusively reflective object.

Formula (6) is based on the paraxial approximation (the argument of the second exponent in (6) is quadratic). It also relies on the assumption of a uniform reflectivity distribution in the illuminated region of the object surface. The above two assumptions are made for convenience; they do not unnecessarily restrict the presented here imaging technique.

The distribution (6) can be imaged by the imaging unit. The spatial intensity distribution at the image plane is:

$$I(x_s, y_s) = |\iint T_m(x_o, y_o)h(x_o - Mx_s, y_o - My_s)dx_o dy_o|^2 \quad (7)$$

Here h is a spatial impulse response of the imaging unit, $(x_s, y_s)$ coordinates in the sensor (light sensitive) plane, and M is the demagnification (inverse magnification) of the imaging unit. The spatial impulse response h takes into account optical and sensor (e.g. PDA) blurring. It is defined on the sensor plane.

If the object surface experiences a tilt, the light field at the close to object plane changes:

$$A_m(x_o, y_o) \propto \left| \begin{array}{l} \int\int \exp[i\phi(x, y)]\exp[i(\beta_x x + \beta_y y)] \\ \exp\left[\frac{\pi i}{\lambda Z_1}((x - x_o)^2 + (y - y_o)^2)\right]dxdy \end{array} \right| \quad (8)$$

$$\beta_x = \frac{4\pi\tan\alpha_x}{\lambda}$$

$$\beta_y = \frac{4\pi\tan\alpha_y}{\lambda}$$

Here, angles $\alpha_x$ and $\alpha_y$ are the tilt components relative to the x and y axes; factor of four in $\beta_x$ and $\beta_y$ includes factor of two which accounts for the double contribution of tilt into the optical length traveled by light on its way to the detector. The optical length is doubly affected because, for example for a part of the surface of interest reproaching the detector, light has, first, to travel more on its way to the surface of interest and, second, has to travel more after reflection at the surface of interest on its way to the detector. It is seen from (8) that the speckle pattern will change due to the tilt.

The change (caused by the tilt) of speckle pattern at the close to object plane causes a change in the spatial intensity distribution at the image plane. The latter change is enhanced, due to the blurring of small speckles with the impulse response of the imaging unit having a large magnification factor. The magnification M can be as high as few hundred. Basically, while the lens is focused on the object or on a plane close to the object, the image of the speckle pattern is varied randomly with tilt of the object (and motion including tilt of the object). Thus, tracking the object motion by imaging the secondary speckle pattern with an imager focused on the object surface or very close to it is a problem.

Additionally, the focusing on a plane being very close to the object of interest can prevent resolving the imaged speckle pattern. For small distances $Z_1$ the average speckle at the imaged plane is small. This is seen from (1), where distance $Z_1$ replaces $Z_2$. If the average speckle size is too small, speckle pattern may not be resolved by the sensor. Therefore, a speckle pattern associated with the aperture of the lens rather than with the object surface may becomes dominant. An average speckle of the latter speckle pattern is $\lambda F_\#$. It coincides with the blurring width of aperture.

However, when the focusing on a plane remote from the object surface is considered, secondary speckle pattern generated by the object becomes dominant and stationary. Defocusing, with respect to the object plane, yields a decrease of the magnification factor M (the decrease may be by one or more orders of magnitude). Defocusing also brings the imaged plane into the far field.

Equations (6) and (7) in the far field become:

$$T_m(x_o, y_o) \propto \int\int \exp[i\phi(x,y)]\exp\left[\frac{-2\pi i}{\lambda Z_2}(xx_o + yy_o)\right]dxdy \propto \quad (9)$$

$$A_m(x_o, y_o)\exp[i\psi(x_o, y_o)]$$

and $$I(x_s, y_s) = \left|\int\int T_m(x_o, y_o)h(x_o - Mx_s, y_o - My_s)dx_o dy_o\right|^2 \quad (10)$$

In (9) the exponent quadratic in coordinates (x,y) is omitted from the integral as this exponent affects phase and amplitude at all points $(x_0, y_0)$ equally. According to (9) and (10), speckle pattern barely changes and shifts as a result of transversal movement. In fact, the transversal movement does not affect the amplitude of the Fourier transform in (9). Also, the magnification of the blur function h in (10) is smaller than it would be with focusing on the object. Axial movement also almost does not affect the speckle pattern. Only a constant phase is added in (9) and the magnification of the speckle pattern is slightly changed.

In the far field, tilting causes shifting of the speckle pattern (as it was mentioned above). This is confirmed by the following equation (11), analogous to equation (8):

$$A_m(x_o, y_o) = \left|\int\int \exp[i\phi(x,y)]\exp[i(\beta_x x + \beta_y y)]\exp\left[\frac{-2\pi i}{\lambda Z_2}(xx_o + yy_o)\right]dxdy\right| \quad (11)$$

$$\beta_x = \frac{4\pi\tan\alpha_x}{\lambda}$$

$$\beta_y = \frac{4\pi\tan\alpha_y}{\lambda}$$

According to (11) tilt can be compensated by a shift of the origin of the coordinate system $(x_o, y_o)$. In other words, tilt introduces into the integral in (11) a phase linear in coordinates (x,y); this phase causes the shift in the Fourier plane $(x_o, y_o)$. This shift is proportional to the tangent of the tilt angle. Equations (8) and (11) tend to describe the light field more accurately for close to normal, with respect to the surface of interest, angles of laser illumination and speckle pattern detection.

Figure 2A:
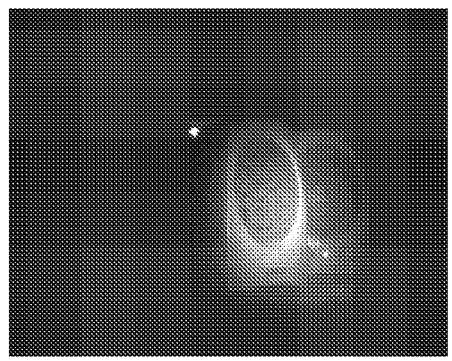

The inventors have experimented with several embodiments of the invented motion detection system. In the first series of experiments, the inventors optically detected and extracted sounds produced by loudspeakers. A photograph of the loudspeakers is shown on FIG. 2A. The loudspeakers were approximately 1 meter away from both a camera (imaging unit) and a coherent light source; they did not move. The camera was Basler A312f; it could capture up to 400 frames per second in a relatively small window of interest. The laser was a frequency-doubled Nd:YAG laser with output power of 30 mW at wavelength of 532 nm. The illuminating laser light was passed through a ×10 lens (with pinhole) positioned side by side with the camera. The illumination spot was about 5 mm in diameter. Both loudspeakers were illuminated by the laser, in sequence. The resulting speckle patterns were imaged with the camera, equipped with a TV lens of a focal length of 16 mm and F-number between 5.6 to 8. The camera was focused on a downward displaced surface being approximately 20 m behind the loudspeakers. The pixel size of the camera PDA was 8.3×8.3 microns. The camera was controlled with Matlab.

In the experiment, the inventors sent an excitation signal of an ascending temporal frequency to the left loudspeaker and an excitation signal of a descending frequency to the right loudspeaker. The camera captured a sequence of 5000 frames in 12.207 seconds. The camera frame rate was 409.6 frames per second (fps), it corresponded to the Nyquist frequency of 205 Hz. In the first frame of the sequence the inventors selected two regions of 10×10 pixels (samples) from regions corresponding to plastic covers of the loudspeakers (not from loudspeakers' membranes). The samples were taken for both the left and the right loudspeaker. For both samples, their positions in other frames were extracted. Then, from these position sequences, spectrograms for sounds of the loudspeakers were calculated. The extraction of sounds thus relied on vibrational motions of walls of loudspeakers' covers. Vibrations changed covers' tilts.

Figure 2B:
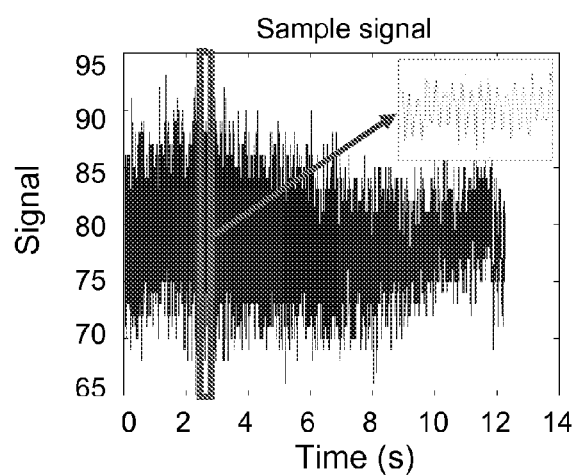

An exemplary temporal sequence of sample position, along one axis, is presented in FIG. 2B. The sample position changed due to motions of the cover of the left loudspeaker. The sample position, in the PDA plane, was extracted by the correlation of sequential frames. The position was normalized for convenient plotting. In the inset a portion of the sample position temporal sequence is shown zoomed.

The position temporal sequence in FIG. 2B was obtained by a search of a shift of the selected sample between sequential frames. For each pair of sequential frames, a sweep through various possible shift values was done; that shift value was selected to be the shift between the two frames of the pair, that produced a maximum correlation between the selected sample being in the first frame and a shifted from it by the shift value 10×10 region in the second frame. Due to noises, not in all frames the selected sample could be found: in some cases there was no 10×10 region in the second frame that would match the selected sample with a high correlation peak. Those frames which did not show a high correlation peak with their previous or subsequent frames had shifts that corresponded to high frequencies and that could be filtered out for the experiments.

From the position temporal sequences of the left and right loudspeakers' covers, the inventors calculated spectrograms. To this end the Matlab function "specgram" was utilized. The function used a default window of 256 frames for calculating "instantaneous" spectra (i.e. for approximating it). In FIG. 2C there is presented a spectrogram reconstructed from the left loudspeaker. The spectrogram is a time-frequency representation of the analyzed signal temporal sequence: in the spectrogram, the horizontal dimension represents time and the vertical dimension represents frequency. Each thin vertical slice of the spectrogram shows the spectrum during a short period of time, using whiteness to stand for amplitude. Whiter areas show those frequencies where the simple component waves have higher amplitude. It is noted, that the spectrogram reconstructed and shown in FIG. 2C matches the loudspeaker excitation signal of the ascending frequency.

In FIG. 2D there is presented a spectrogram reconstructed from the image sequence containing the right loudspeaker. For the reconstruction the same digital processing was used as in the previous example. Here as well the spectrogram matches the excitation signal sent to the loudspeaker.

In another series of experiments the inventors applied their technique for extraction of human voice signals (singing of one of the inventors) played on the loudspeakers. As in the previous series of experiments, they illuminated the loudspeakers with coherent light and imaged them with a camera focused on a removed plane.

The obtained two sequences of images were processed in several steps performed on an appropriately programmed computer. In the first step, a sample was selected and a time dependence of its position in the image (PDA) plane was determined (for each of two sequences). In the second step, a low pass filtering was applied to the sample position time dependence and the filtered signal was subtracted from the dependence (for each of two sequences); frequencies corresponding to the inventor's voice were kept in the difference. The signals were purified: only those images (sequence frames), which provided a high likelihood (signal-to-noise ratio, more than 10) of finding the sample in these images, were kept. The signals could be enhanced by using interpolation prior to shift finding for each signal and using larger samples. As well, they could be enhanced by iterating the process of finding the high SNR samples, by increasing sample pixel size in the iteration process. Likewise, shifts finding can also be iterated. Even without the additional enhancement obtained samples vibrations were indicative of the singer's voice sounds. This was verified by transforming the reconstructed signals into suitable electrical signals, exciting the loudspeakers with the electrical signals, and listening to the produced sounds.

In another series of experiments the inventors have optically detected and extracted human speech signals, produced by an experiment participant (one of the inventors). The participant not only talked, but also moved during the experiments (the loudspeakers from the previous experiments did not move for reasons unconnected with production of sound). For sound detection, imaging of speckle pattern originating from one of the participant's throat, face (in particular cheekbone), back of the head and other regions of the head was, in various experiments, performed. The imager (camera) was focused on a forward displaced plane being closer to the camera than the source of the speckle pattern. In experiments, the inventors used the same Basler A312f camera with a matrix of 782×582 pixels. Shutter rates were between 40 to 100 microseconds, in frequency units between 25 KHz to 10 KHz, the gain (internal parameter of the camera) was 192. The camera was used with a Computar telecentric lens of the focal length 55 mm and F-number 2.8. The camera speed was almost independent of a number of pixels in a used region of the matrix. The inventors used samples of sizes 20×20 and 20×40 pixels. A Suwtech double Nd-YAG laser at power between 1 and 20 mW and wavelength 532 nm was used for creating speckle patterns.

In FIGS. 3A and 3B there are shown 20×20 samples of two sequentially taken speckle patterns. In FIG. 3C there is presented a defocused image of the inventor. The image is defocused, since the camera was focused on a forward displaced plane. The speckle pattern originates from the inventor's throat.

Figure 3D:
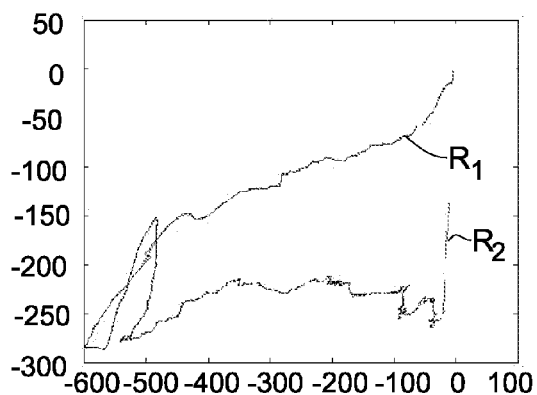
Figure 3E:
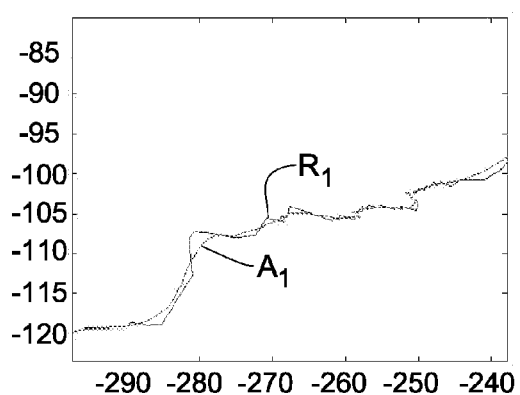

Speckle pattern images were sequentially correlated for sample shift finding. The found differential displacements of the sample were accumulated. In FIG. 3D there are presented two examples $R_1$ and $R_2$ of the sample trajectory on the imaging plane (i.e. PDA). A part of the upper trajectory and its sliding average are shown in a greater detailed view in FIG. 3E. The lines are denoted $R_1$ and $A_1$, respectively. The slidingly averaged real trajectory, i.e. the trajectory $A_1$, corresponds to the person's principal movement (mostly tilt). Vibrations of real trajectory $R_1$ around the filtered trajectory $A_1$ correspond to the person's speech.

Figure 3F:
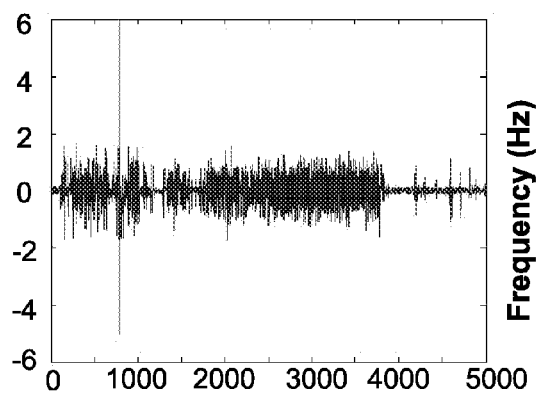

In FIG. 3F there is shown a difference between the real and smoothed trajectories of the speckle pattern. Deviation of the trajectory from its sliding average can fully or partially correspond to person's acoustical movements (tilting vibrations). Thus, the sliding voice spectrum of the difference between real and smoothed trajectories is indicative of the human speech. The sliding spectrum can be found by slidingly transforming the deviation temporal dependence into the frequency domain and selecting from this domain the voice frequency band (e.g. the telephony voice frequency band ranging from approximately 300 Hz to 3400 Hz). The sliding time interval on which the transformation is done may be 10 ms. For the detection and extraction of speech, shift of the speckle pattern in any direction on the PDA plane can be utilized.

Figure 3G:
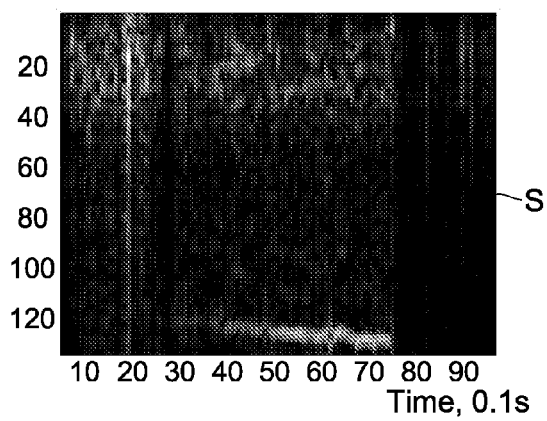

In FIG. 3G there is shown a spectrogram calculated from the time evolution of the speckle pattern position on the PDA. The vertical axis shows sound frequency in Hz. The horizontal axis shows time, in tenths seconds (0.1 s). The person screamed during the imaging; the scream is reflected by band S being at relatively high frequencies in the spectrogram (approximately 120 Hz).

The inventors performed simulations for a design of several more speech detection setups. In the simulations, they used 2 cm as a value of the diameter of illumination spot (i.e. D=2 cm).

For wavelength of 400 nm, focal length F=10 mm (a fairly small value) and f-number of F#=1 (i.e. aperture diameter of φ=10 mm), a maximal object distance was calculated to be approximately $Z_2^{(max)}$=500 m. Decreasing aperture diameter φ (increasing the f-number F#) will decrease $Z_2^{(max)}$. A suitable camera-in-focus plane distance was calculated to be between 20 cm and 6 m. The calculation was done so that the far field condition was preserved. For wavelength of 2 microns and f-number of F#=1 the inventors obtained maximal object distance $Z_2^{(max)}$ of about 100 m. A suitable interval for the in-focus plane distance $Z_3$ did not change.

For wavelength of 400 nm, focal length F=1000 mm (a fairly large value) and f-number F#=1 (i.e. aperture diameter φ=1000 mm), the calculated maximal object distance $Z_2^{(max)}$ was about 50 km, while the calculated minimal in-focus plane distance $Z_3^{(max)}$ was about 3 km. Again, these values were calculated for preservation of the far field approximation. Also, a maximal in-focus plane distance can be estimated such that the far field condition is preserved. For wavelength of 2 microns, the inventors obtained for the same conditions (D=2 cm and φ=1000 mm) that the maximal object distance is $Z_2^{(max)}$=10 km.

Figure 4A:
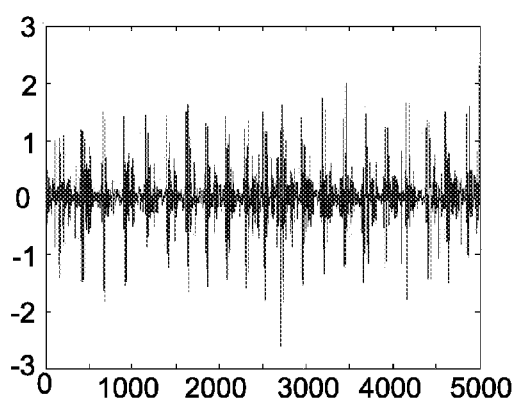
FIGS. 4A and 4B illustrate the following: (a) Vibrations of the speckle pattern position caused by heart beat; (b) The spectrogram of the signal of 3A.
Figure 4B:
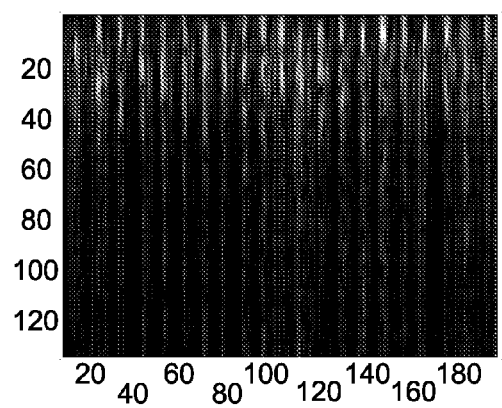

In yet another series of experiments the inventors have used their technique to detect the assistant's heart beats. To this end, they imaged speckle pattern originating from the assistant's chest, covered with a cloth. In FIG. 4A there is shown a time dependence of the extracted by correlation sample shift. The time axis is drawn in units, five thousands (5000) of which correspond to 20 seconds. The signal (the shift of the correlation peak) is measured in pixels (or in pixel units). In FIG. 4B there is shown a spectrogram of the signal. The heart beats are well distinguishable. Thus, the invented technique allows contactless monitoring of the human heart rate. This contactless monitoring can be utilized in hospitals for monitoring patients, in rescue operations for detecting living signs of victims of the accidents, and in sports and physical training. The heart beats can also be contactlessly detected by imaging of a speckle pattern produced at hand joint.

The inventors' technique can be used not only for detection of presence of heart beats, but also for determination of such medical parameters as heart beats rate (i.e. pulse) and blood pressure and for characterization of physical strain, experienced by an individual (a human or an animal). This should become useful in medicine, veterinary medicine, and agriculture. Moreover, the inventors' technique can be used for obtaining optical cardiograms (OCGs). An OCG can be built from a sequence of images of a stationary speckle pattern, wherein these images are indicative of vibrations associated with vibrations of heart and the sequence is indicative of heart beats. The latter condition means that the sequence, preferably, has to be taken with a rate exceeding the Nyquist rate for heart beats. OCG can be used not only for determining health conditions, but also for authentification, as OCG appears to be an individualized repeatable characteristic.

The inventors have performed a series of experiments in which they used OCG for determination of pulse and characterization of physical strain. In the experiment, they illuminated experiment participants' body parts with a Nd:YAG laser working at wavelength of 532 nm and imaged reflected coherent speckle patterns with a digital camera model Pixel Link A741. The camera and the laser were positioned side by side. The participants were separated by a distance of about 1 m from the camera. The camera was focused on a far range of about 20 m. For vibration extraction, spatial regions (samples) of 128 by 128 pixels were utilized. The correlation plane was 256×256 pixels; the correlation peak appeared somewhere close to its center.

Figure 5A:
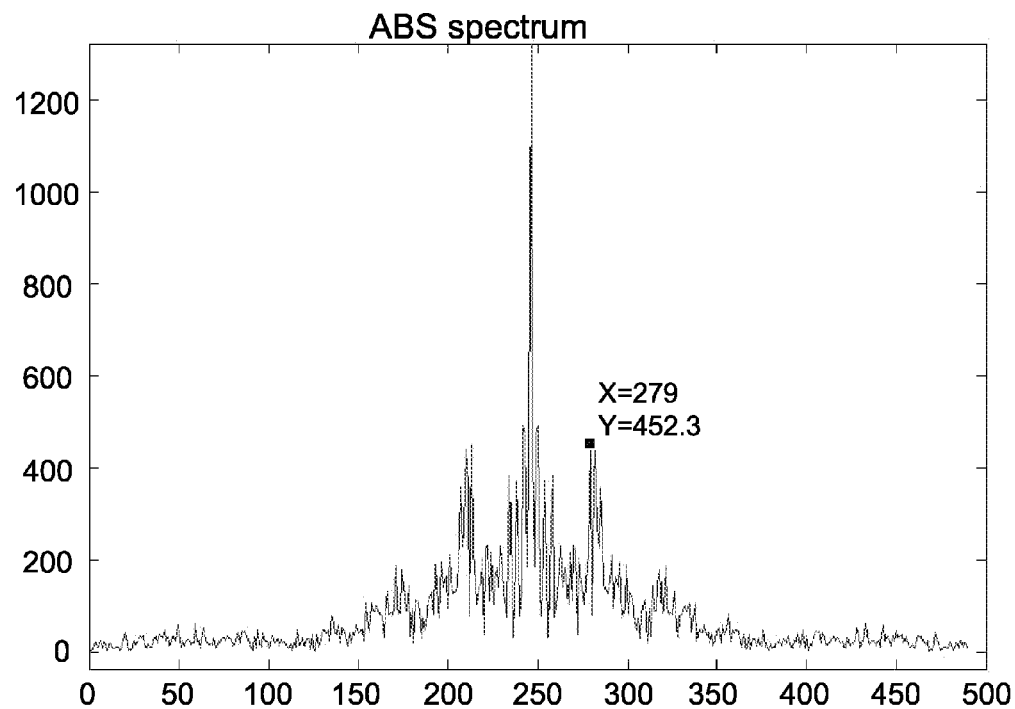
FIGS. 5A-5F show various Optical Cardiograms, obtained with the technique of the invention, in frequency domain (the graphs middle marks correspond to the zero frequency).

Referring to FIG. 5A there is shown a frequency representation (Fourier transform) of a time-dependence of a coordinate of the same sample found in a sequence of speckle pattern images. In other words, there is shown the Fourier transform of OCG or OCG in frequency domain. Speckle patterns originated from a Subject's hand joints. Images were taken at a rate 20 Hz. Five hundred (500) images (frames) were taken and the resulting spectral resolution therefore was 1/(500/20)=0.04 Hz. The Fourier transform was performed over a sequence of 490 frames; these resolution units were used for frequency axis in the FIG. 5A. The frequency is zero at the central, highest, peak of the Fourier transform, positioned at 245 units in the plot (the Fourier transform is shifted from 0, since it is plotted in the plot units). The plot is symmetric, because the temporal signal is real. The next highest spectral peak is located at mark 279. This peak corresponds to heart beats occurring with a rate 0.04 (279−245) Hz=1.36 Hz. A control measurement was performed with Polar Clock; its result was 1.33 pulses/sec.

Figure 5B:
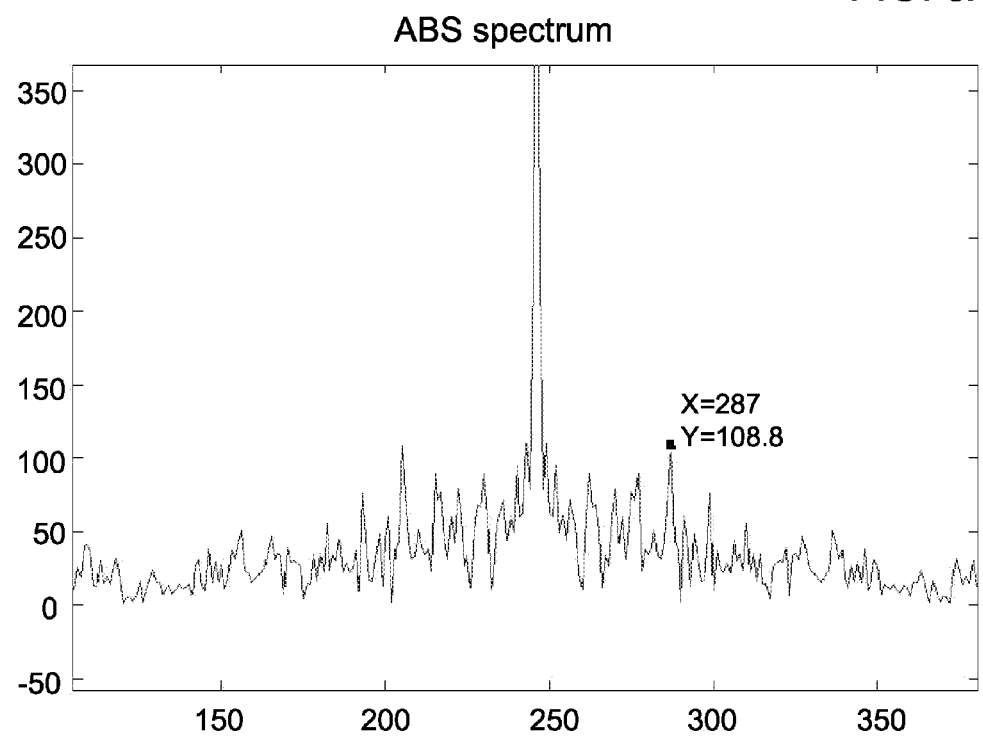

The pulse rate measurement was repeated for the same Subject (#1) at physical strain. The respective Fourier transform is shown in FIG. 5B. This time the highest non-central peak was at a mark 287 and pulse rate 0.04 (287−245) Hz=1.68 Hz. The respective Polar clock measurement was 1.783 (pulses per second).

Figure 5C:
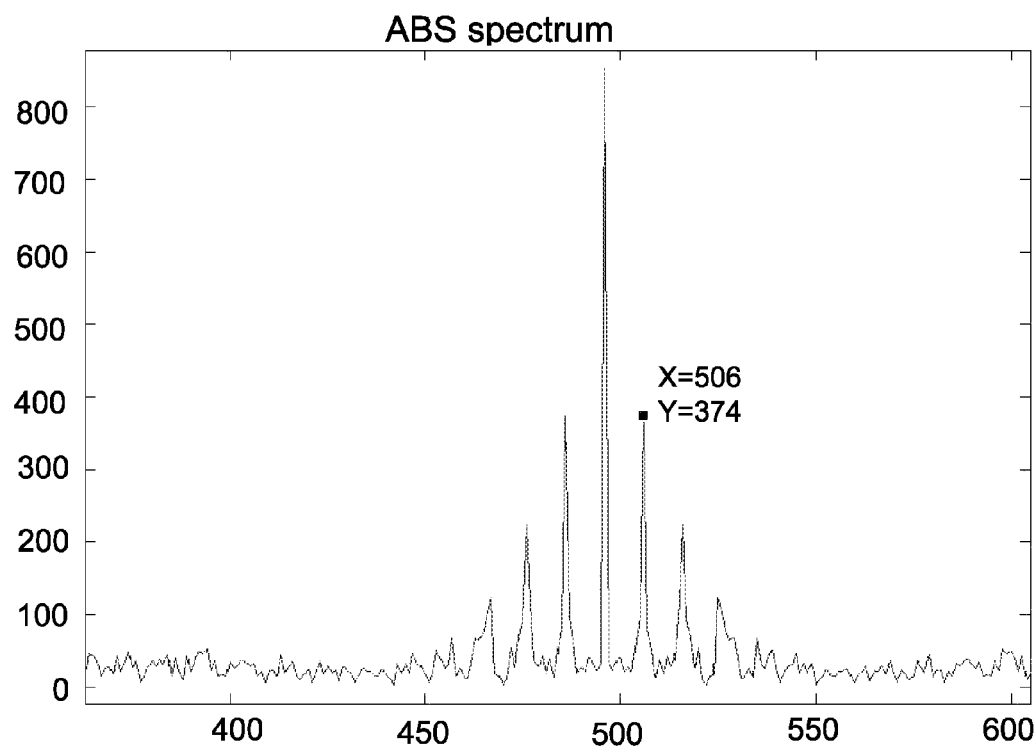
Figure 5D:
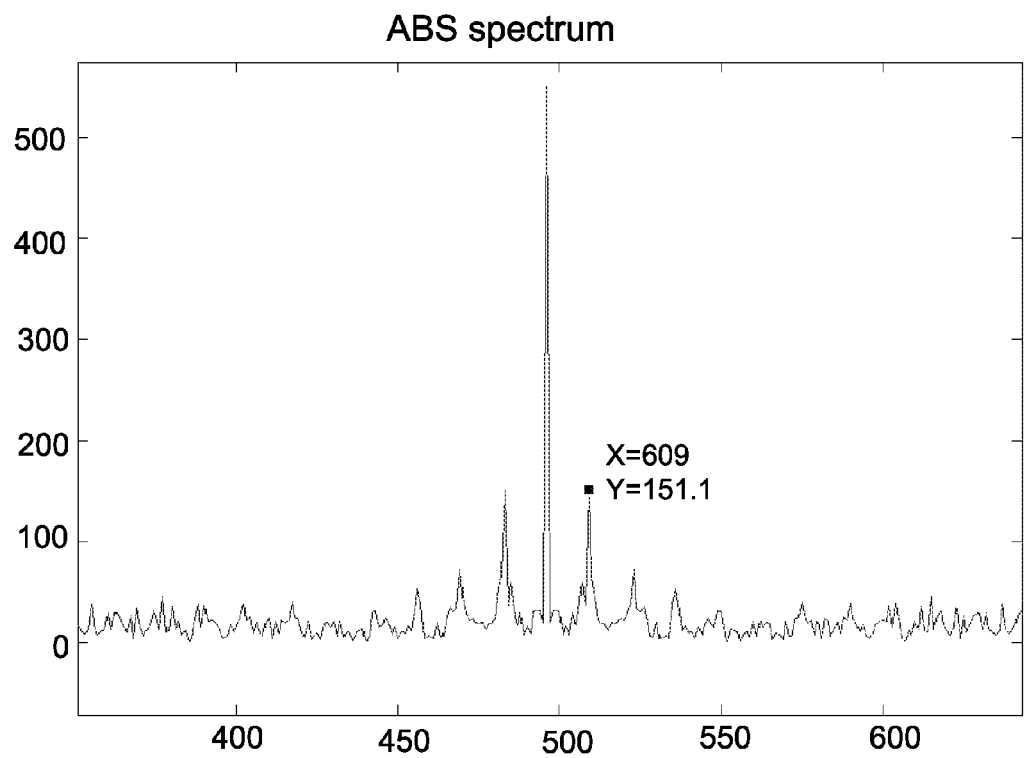
Figure 5E:
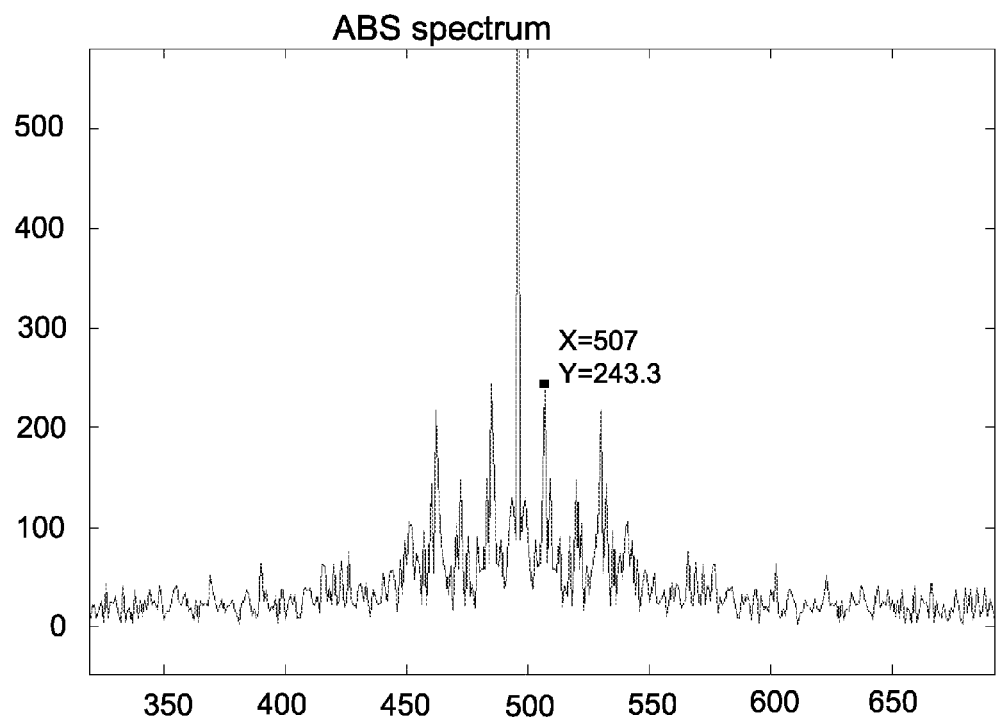
Figure 5F:
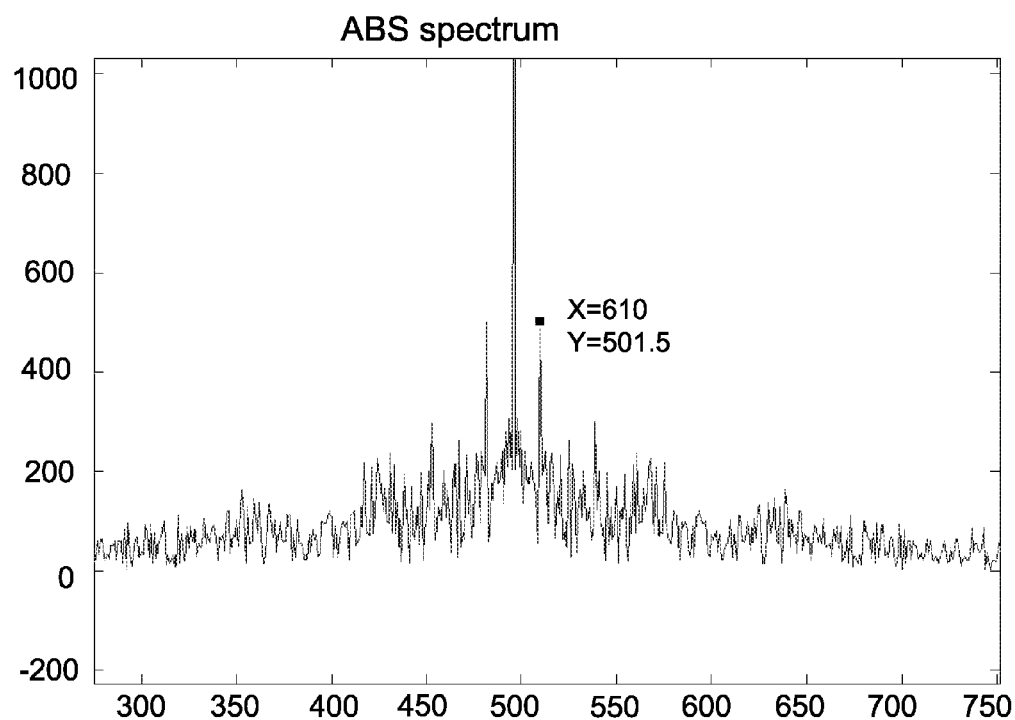

Four next measurements were performed at a rate of 100 Hz; 1000 images were taken in time windows of 10 seconds. In the first measurement of these four, the control Polar Clock measurement gave the result of 1.033 pulses per second, for a Subject #2 at rest. Since the spectral resolution was 1/(1000/100)=0.1 Hz and 990 frames participated in the spectral computation, the peak had to appear at mark 1.033/0.1+495=505.3. In fact, in FIG. 5C the peak appears at mark 506. In the second measurement, performed for Subject #3 experiencing physical strain after physical activity, the Polar Clock measurement was 1.433 pulses per second; therefore the peak had to appear at mark 1.433/0.1+495=509.3. The peak appeared at mark 509 (FIG. 5D). In the next measurement the Polar Clock result was 1.216 Hz, for a Subject #3 at rest; therefore the peak was anticipated at mark 1.216/0.1+495=507.2. The peak was obtained at mark 507 (FIG. 5E, this time the speckle pattern originated from Subject's throat). In the last measurement of the four, the Polar Clock measurement was 1.5 pulses per second, for Subject #3 at physical strain, and therefore the peak was anticipated at mark 1.5/0.1+495=510. Indeed, inventors received the peak at mark 510 (FIG. 5F, the speckle pattern originated from Subject's throat).

Thus, it is seen that the inventor's technique is capable of being used for contactless heart rate measurement.

Figure 6A:
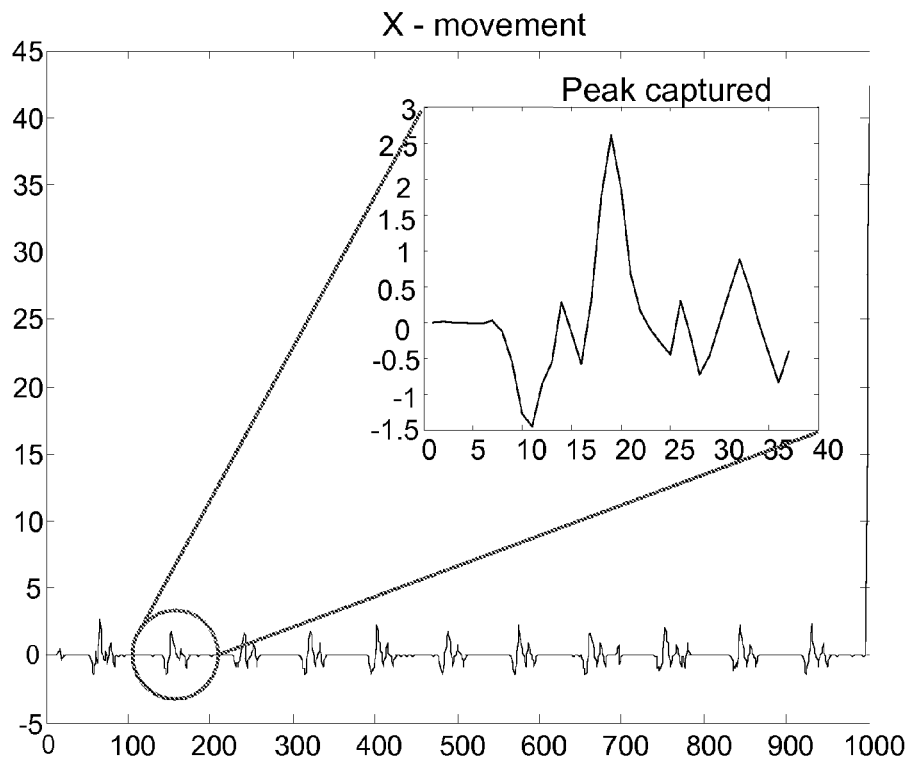
FIGS. 6A-6F show various Optical Cardiograms, obtained with the technique of the invention, in time domain.
Figure 6B:
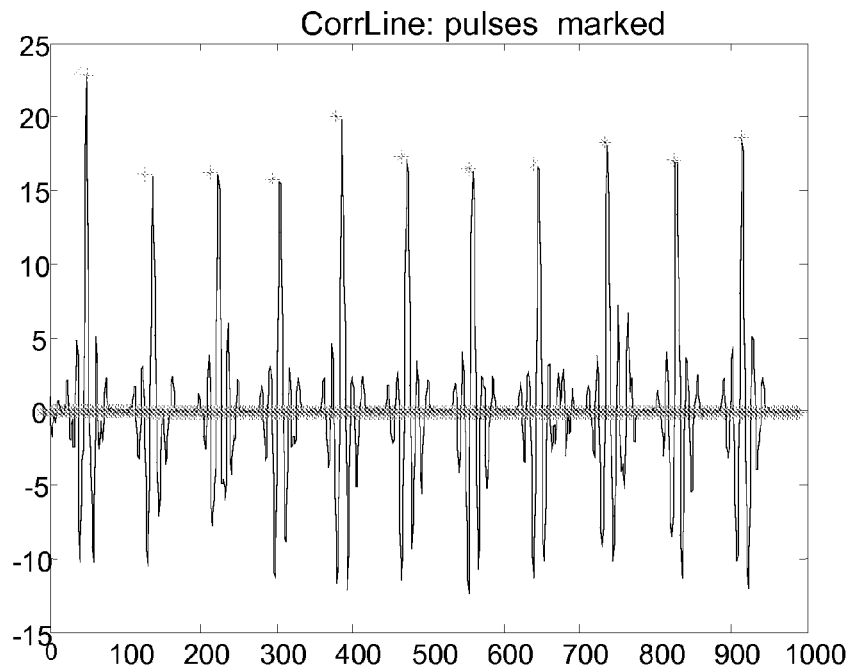
Figure 6C:
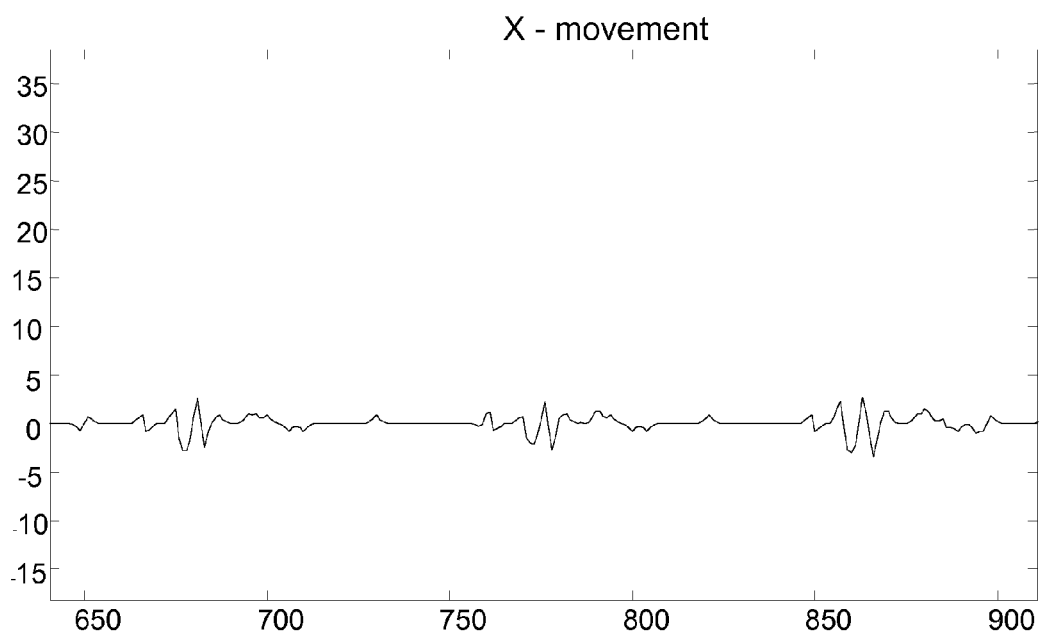
Figure 6D:
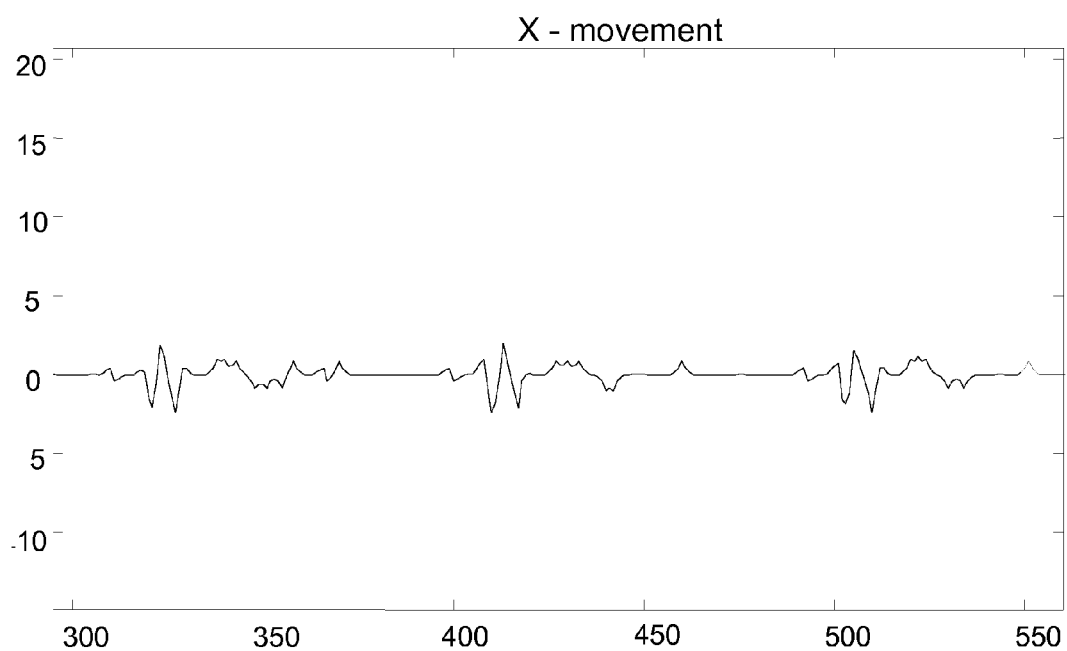
Figure 6E:
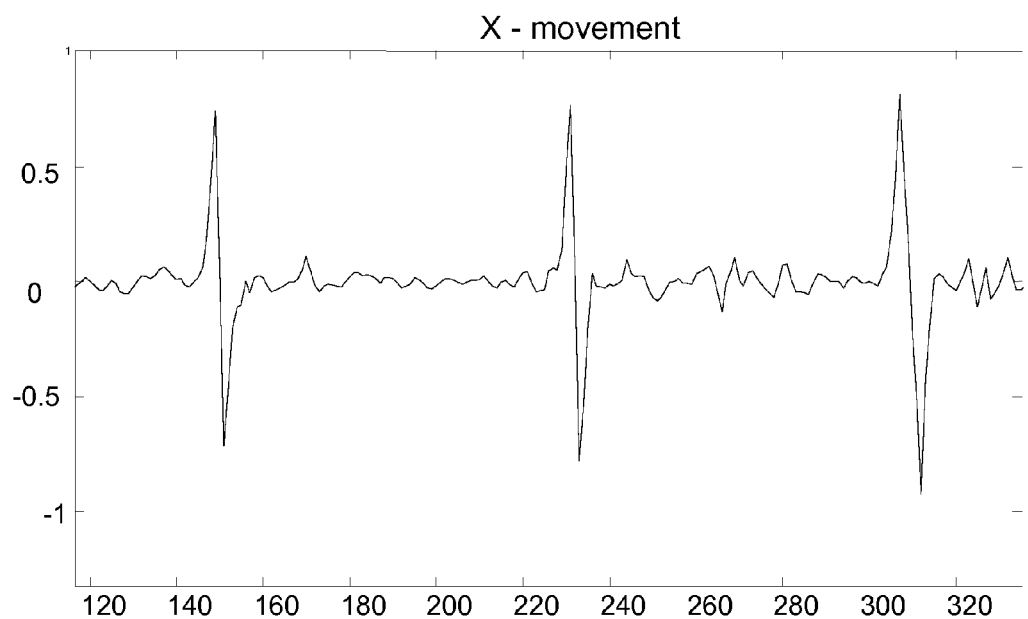
Figure 6F:
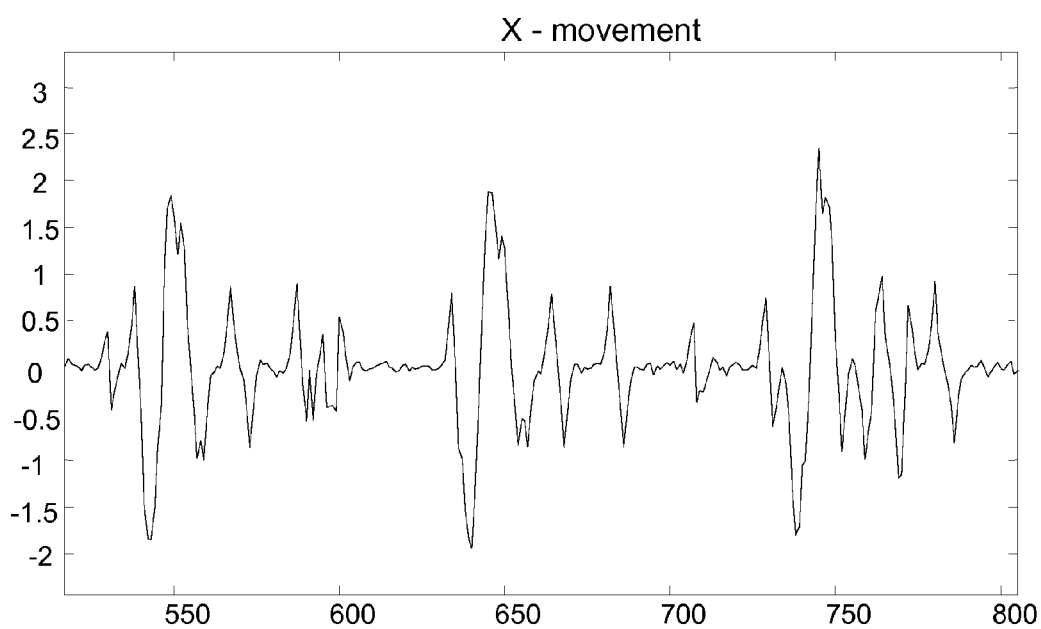

Further, the inventors have performed a series of experiments that showed that OCG is highly individualized characteristics. The experiments were performed with the same setup used in the examples of FIGS. 5C-5F. The imaging rate was 100 Hz. In FIG. 6A there is shown an OCG in time domain of a Subject #4, with a single period of this OCG enlarged in the inset. This single period can be sufficient for use as signature, as the OCG generally repeats itself in other periods. In FIG. 6B there is shown an OCG of a Subject #5. This OCG also generally repeats itself. The signatures of Subjects #4 and #5 look different; and beats of Subject #5 in general have a high correlation with each other and a low correlation with beats of Subject #4. Beats of each subject preserve their unique temporal shape. In FIGS. 6C and 6D there are presented OCGs of a subject #6 at rest in different days. The signatures are alike, despite the time period passed between the measurements. In FIGS. 6E and 6F there are presented OCGs of Subjects #7 and #8. Different Subjects have indeed different signatures.

Hence, OCG appears to carry a unique signature of a person as for example finger prints or retina prints. OCG therefore can be used as an entrance key to secured areas. On the other hand, OCG also carries information about person's medical and/or strain condition. This for example can be used in a lie detector: when a person lies, his OCG will change and this can be detected with the technique of the present invention.

Similarly to the above examples, the technique of the inventors can be used for biomedical imaging of a fetus. The vibrations of fetus may be excited by ultrasound. The reflected from fetus sound waves can be imaged by the technique of the inventors in addition or rather than acoustically.

Somewhat similarly to the OCG example, the technique of the inventors can be used for diagnostics and recognition or authentification of vehicles. An imperfection of car engine work often results in specific to this imperfection sound or disruption of the engine's sound; many drivers and mechanics use these specifics to find the cause of the imperfection. However, such diagnosing by listening is difficult, partly because of the noise done by engine, partly because of the limited hearing of humans. Also, the source of the sound often may not be easily localized. Using the technique of the inventors allows detecting and characterizing various engine and vehicle sounds, even while they still are weak for the human ear; and it also allows localizing the sounds' sources. Also, the optical detection allows achieving a higher precision over the acoustical detection. Thus, the technique of the inventors will be useful not only for establishing the source of failures, but also for preventing them at the early stages. This entails a possibility of a better maintenance of vehicles.

In view of the above, applications of the technique of the inventors to the diagnostics of vehicles can use one or more sequence of images of a stationary speckle pattern, wherein these images are indicative of vibrations associated with a vehicle and the sequence is indicative of a vehicle operation. These images may be (defocused) images of a vehicle's engine part or parts. The images may also be (defocused) images of a vehicle's wheel system or transmission. The vehicle may be operated with idling engine; the vehicle may have wheels which may be or may not be rotated by the engine. The sequence may be stored in a memory, such as memory of a general purpose computer, or memory of a specialized device, or a memory carrier (e.g. an operative memory, a video memory, a compact disc, an optical disc, a hard drive disc, a flash memory device, etc). The vehicle itself may be a car, a ship, a locomotive, an air plane, a helicopter, or any other which operation or which engine operation is associated with mechanical vibrations. The vehicle diagnostics may also utilize a set of image sequences taken at different engine rates and/or for different vehicle parts.

The technique of the inventors can also be used in home land security applications. For example, it can be utilized for distinguishing vehicles, e.g. cars (for these purposes, license plates are currently used). In particular, it can be utilized for finding camouflaged vehicles. Similarly appearing vehicles can be distinguished for example by their engines, which have different vibrating signatures. In motion, though that the engine is hidden in the vehicle's inside, vibrations are transferred to the vehicle's outside, and therefore the vibrations can be found by the defocused imaging of speckle patterns formed on vehicle's exterior (e.g. hood, body, wind shields).

Those skilled in the art will readily appreciate that various modifications and changes can be applied to the embodiments of the invention as hereinbefore described without departing from its scope defined in and by the appended claims.

The invention claimed is:

1. A method for use in motion detection of an object, the method comprising:
providing a system comprising a source of a beam of coherent light and an imaging system capable of being focused on a plane displaced from an intersection of the beam and a field of view of the imaging system and being in a far field from said intersection; operating said system for illuminating an object by the beam of coherent light, and imaging the coherent speckle pattern, originated at and propagating from the object, while focusing the imaging system on a plane being in a far field of the object and being located further than $D^2/4\lambda$ from the object, D and $\lambda$ being respectively a size and a wavelength of the speckle pattern at the object.

2. The method of claim 1, wherein said displaced plane is located between the imaging system and the object, or is located further from the imaging system than the object.

3. The method of claim 1, wherein the object is moving.

4. The method of claim 3, wherein the movement is associated with a vibration of at least one of the following: vibration of a living body's part, and a cloth on a living body.

5. The method of claim 3, wherein the movement is associated with a vibration, said vibration corresponding to at least one of the following: a speech, a sequence of heart beats, a heart beat resolved to a heart beat's structure, and a blood pressure.

6. The method of claim 5, wherein the imaging is repeated at least two times for obtaining a sequence of at least two said speckle pattern images.

7. The method of claim 6, comprising: processing image of the object obtained by said imaging of the coherent speckle pattern propagating from the object, said processing comprising at least one of the following: extracting the speech from said sequence; extracting the sequence of heart beats, extracting the heart beat's structure, extracting the heart beat's structure and comparing it with a heart beat's structure of the same or different heart.

8. The method of claim 3, wherein the movement is associated with a vibration of a living body's part, said vibration corresponding to a speech.

9. The method of claim 3, wherein the movement is associated with a vibration of a living body's part, said living body's part being at least one of a hand joint, a chest, a throat, a temporal fossa, a throat, a cheekbone, a head, a stomach.

10. The method of claim 3, wherein the movement is associated with a vibration, said vibration being that of a vehicle's part.

11. The method of claim 10, wherein said vehicle's part comprises at least one of vehicle interior or exterior parts.

12. The method of claim 10, wherein said vehicle's part is a part of vehicle's engine.

13. The method of claim 1, comprising: determining at least one shift between regions of the object which appear in at least first and second images of the object, each of said regions including the stationary speckle pattern formed by light originated at the same region of the object and imaged by focusing the imaging system on the plane which is displaced from the object and located in the far field of the object; and determining motion of the object along transverse, axial, and tilt dimensions.

14. The method of claim 1, comprising determining a shift between regions of the object which appear in first and second images of the object, each of said regions including the stationary speckle pattern formed by light originated at the same region of the object and imaged by focusing the imaging system on the plane which is displaced from the object and is located in the far field of the object.

15. A system for use in motion detection, the system comprising:
a source of a beam of coherent light and an imaging system, said imaging system being capable of being focused on a plane displaced from an intersection of the beam and a field of view of the imaging system and being in a far field from said intersection; and a processing unit associated with said imaging system, said processing unit being configured and operable to determine a shift between two images of a speckle pattern originated at the intersection location, said processing unit being configured for communication with a device comprising a memory unit, comprising data indicative of a sequence of images of a stationary coherent speckle pattern originated at a subject, being indicative of the subject's heart beats and/or heart beat structure, said sequence being thereby enabled for use in determination of at least one physiological parameter.

16. The system of claim 15, wherein said plane is located either between the imaging system and the intersection location or is located further from the imaging system than the intersection location.

17. A system of claim 15, wherein said processing unit is configured for determining at least one of the following: a sequence of shift values between the images in the sequence of images of the stationary speckle pattern; and a spectrogram of a sequence of shift values.

18. The system claim 15, wherein said plane is located further than $D^2/4\lambda$ from the intersection location, D and $\lambda$ being respectively a size and a wavelength of a speckle pattern originated at the intersection location, said plane thereby being in a far field of the intersection location.

19. The system of claim 15, wherein the processing unit is configured to operate the imaging system to repeat imaging at least two times for obtaining a sequence of at least two images of the speckle pattern.

20. The system of claim 15, wherein the processing unit is configured for processing an image of the intersection location obtained by imaging of the coherent speckle pattern propagating from the intersection location, said processing comprising at least one of the following: extracting a speech from said sequence; extracting the sequence of heart beats, extracting a heart beat's structure, extracting a heart beat's structure and comparing it with a heart beat's structure of the same or different heart.

21. A system for use in for use in motion detection, the system comprising:

a source of a beam of coherent light and an imaging system, said imaging system being capable of being focused on a plane displaced from an intersection of the beam and a field of view of the imaging system; and a processing unit associated with said imaging system, said processing unit being configured and operable to determine a shift between two images of a speckle pattern originated at the intersection location, wherein said processing unit is configured for communication with a device comprising a memory unit comprising data indicative of a sequence of images of a stationary speckle pattern originated at a subject, said sequence being indicative of the subject's speech.

22. The system of claim 21, wherein said data comprises at least one of the following: the sequence of images of the stationary speckle pattern; and a sequence of shift values between the images of the stationary coherent speckle pattern, said sequence being indicative of the speech.

23. The system of claim 21, wherein said sequence comprises an image of at least one of a throat, a cheekbone, a head.

24. The system of claim 21, comprising a processor for determining a spectrogram of said sequence of shift values, said sequence being taken with a rate of 2 kHz or higher.

25. The system of claim 21, wherein said plane is located either between the imaging system and the intersection location or is located further from the imaging system than the intersection location.

26. The system of claim 21, wherein said plane is located further than from the intersection location, and being respectively a size and a wavelength of a speckle pattern originated at the intersection location, said plane thereby being in a far field of the intersection location.

27. The system of claim 21, wherein the processing unit is configured to operate the imaging system to repeat imaging at least two times for obtaining a sequence of at least two images of the speckle pattern.

28. The system of claim 21, wherein the processing unit is configured for processing an image of the intersection location obtained by imaging of the coherent speckle pattern propagating from the intersection location, said processing comprising at least one of the following: extracting a speech from said sequence; extracting the sequence of heart beats, extracting a heart beat's structure, extracting a heart beat's structure and comparing it with a heart beat's structure of the same or different heart.

29. A system for use in for use it motion detection, the system comprising:

a source of a beam of coherent light and an imaging system, said imaging being capable of being focus on a plane displaced from an intersection of the beam and a field of view of the imaging system; and a processing unit associated with said imaging system, said processing unit being configured and operable to determine a shift between two images of a speckle pattern originated at the intersection location, wherein said processing unit is configured for communication with a device comprising a memory comprising data indicative of a sequence of images of a stationary speckle pattern originated at a vehicle, the images being indicative of vibrations associated with the vehicle and the sequence being indicative of the vehicle operation.

30. The system of claim 29, wherein said plane is located either between the imaging system and the intersection location or is located further from the imaging system than the intersection location.

31. The system of claim 29, wherein said plane is located further than from the intersection location, and being respectively a size and a wavelength of a speckle pattern originated at the intersection location, said plane thereby being in a far field of the intersection location.

32. The system of claim 29, wherein the processing unit is configured to operate the imaging system to repeat imaging at least two times for obtaining a sequence of at least two images of the speckle pattern.

33. The system of claim 29, wherein the processing unit is configured for processing an image of the intersection location obtained by imaging of the coherent speckle pattern propagating from the intersection location, said processing comprising at least one of the following: extracting a speech from said sequence; extracting the sequence of heart beats, extracting a heart beat's structure, extracting a heart beat's structure and comparing it with a heart beat's structure of the same or different heart.

34. A method for use in motion detection of an object, the method comprising:

providing a system comprising a source of a beam of coherent light and an imaging system capable of being focused on a plane displaced from an intersection of the beam and a field of view of the imaging system;

operating said system for illuminating an object by the beam of coherent light, and imaging the coherent speckle pattern, originated at and propagating from the object, by an imaging system being focused on a plane displaced from the object; and determining at least one shift between regions of the object which appear in at least first and second images of the object, each of said regions including the stationary speckle pattern formed by light originated at the same region of the object and imaged by focusing the imaging system on the plane which is displaced from the object.

35. The method claim 34, wherein said plane is located further than $D^2/4\lambda$ from the object, D and $\lambda$ being respectively a size and a wavelength of the speckle pattern at the object.

36. The method of claim 34, comprising utilizing the determined at least one shift between said regions of the object, and determining motion of the object along transverse, axial, and tilt dimensions.

37. The method of claim 36, wherein the object is moving.

38. The method of claim 37, wherein the movement is associated with a vibration of at least one of the following: vibration of a living body's part, and a cloth on a living body.

39. The method of claim 38, wherein the movement is associated with the vibration corresponding to at least one of the following: a speech, a sequence of heart beats, a heart beat resolved to a heart beat's structure, and a blood pressure; a vibration of a living body's part being at least one of a hand joint, a chest, a throat, a temporal fossa, a throat, a cheekbone, a head, a stomach; a vibration of a vehicle's part comprises at least one of vehicle interior or exterior parts.

40. The method of claim 39, wherein the imaging is repeated at least two times for obtaining a sequence of at least two said speckle pattern images.

* * * * *